United States Patent [19]

Montgomery et al.

[11] 4,387,228

[45] Jun. 7, 1983

[54] PROCESS FOR THE PRODUCTION OF (±)3-DEAZAARISTEROMYCIN

[75] Inventors: John A. Montgomery; Sarah D. Clayton, both of Birmingham, Ala.

[73] Assignee: Southern Research Institute, Birmingham, Ala.

[21] Appl. No.: 302,845

[22] Filed: Sep. 16, 1981

[51] Int. Cl.$^3$ .......................................... C07D 471/04
[52] U.S. Cl. ..................................... 546/118; 424/256
[58] Field of Search ......................... 424/256; 546/118

[56] References Cited

U.S. PATENT DOCUMENTS

| | | | |
|---|---|---|---|
| 3,891,660 | 6/1975 | Denzel et al. | 546/118 |
| 3,919,193 | 11/1975 | Mian et al. | 424/180 |
| 4,148,888 | 4/1979 | Cantoni et al. | 424/180 |
| 4,210,639 | 7/1980 | Chiang et al. | 424/180 |
| 4,315,000 | 2/1982 | Cook | 424/180 |

*Primary Examiner*—Ethel G. Love
*Attorney, Agent, or Firm*—John S. Roberts, Jr.

[57] ABSTRACT

A process for the production of (±)3-deazaaristeromycin, which is also known as (±)-4-amino-1-[(1α, 2β, 3β, 4α)-2,3-dihydroxy-4-(hydroxymethyl)-cyclopentyl]imidazo[4,5-c]pyridine, which comprises:

(1) reacting 2,4-dichloro-3-nitropyridine with (±)(1,4/2,3)-4-amino-2,3-dihydroxy-1-cyclopentanemethanol to give (±)-(1,4/2,3)-4-(3-nitro-2-chloro-4-pyridylamino)-2,3-dihydroxy-1-cyclopentanemethanol (compound II);

(2) subsequently reducing compound II to (±)-(1,4/2,3)-4(3-amino-2-chloro-4-pyridylamino)-2,3-dihydroxy-1-cyclopentanemethanol (compound III);

(3) acid catalyzed cyclization of compound III to (±)-4-chloro-1-(1α, 2β, 3β, 4α)-2,3-dihydroxy-4-(hydroxymethyl)cyclopentyl)imidazo[4,5-c]pyridine (compound IV);

(4) displacing the chloro group of compound IV to produce (±)-4-hydrazino-1-(1α, 2β, 3β, 4α)-2,3-dihydroxy-4-(hydroxymethyl)cyclopentyl)-imidazo[4,5-c]pyridine (compound V);

(5) cleaving said hydrazino compound V to produce (±)-4-amino-1-[(1α, 2β, 3β, 4α)-2,3-dihydroxy-4-(hydroxymethyl)cyclopentyl]imidazo[4,5-c]-pyridine (compound VI).

1 Claim, No Drawings

PROCESS FOR THE PRODUCTION OF (±)3-DEAZAARISTEROMYCIN

This invention relates to a process for the production of (±)3-deazaaristeromycin, which is also known as (±)-4-amino-1-[(1α,2β,3β,4α)-2,3-dihydroxy-4-(hydroxymethyl)-cyclopentyl]imidazo[4,5-c]-pyridine, which comprises:

(1) reacting 2,4-dichloro-3-nitropyridine with (±)(1,4/2,3)-4-amino-2,3-dihydroxy-1-cyclopentanemethanol to give (±)-(1,4/2,3)-4-(3-nitro-2-chloro-4-pyridylamino)-2,3-dihydroxy-1-cyclopentanemethanol (compound II) in an equimolar reaction in the presence of triethanolamine;

(2) subsequently reducing compound II to (±)-(1,4/2,3)-4(3-amino-2-chloro-4-pyridylamino)-2,3-dihydroxy-1-cyclopentanemethanol (compound III) by hydrogen and Raney nickel catalyst;

(3) acid catalyzed cyclization of compound III to (±)-4-chloro-1-(1α,2β,3β,4α)-2,3-dihydroxy-4-(hydroxymethyl)cyclopentyl)imidazo[4,5-c]pyridine (compound IV) with triethylorthoformate in N,N-dimethylacetamide with an acid catalyst;

(4) displacing the chloro group of compound IV with hydrazine to produce (±)-4-hydrazino-1-(1α,2β,3β,4α)-2,3-dihydroxy-4-(hydroxymethyl)cyclopentyl)-imidazo[4,5-c]pyridine (compound V);

(5) cleaving said hydrazino compound V to produce (±)-4-amino-1-[(1α,2β,3β,4α)-2,3-dihydroxy-4-(hydroxymethyl)cyclopentyl]imidazo[4,5-c]-pyridine (compound VI) under a nitrogen blanket with Raney nickel under a reflux (1 hour).

The present invention pertains to the synthesis of the carbocyclic analog of 3-deazaadenosine represented by the following formula:

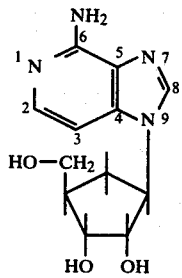

(±)-3-Deazaaristeromycin

It has been found that this compound is useful as an antiviral agent and is a potent inhibitor of adenosylhomocysteine hydrolase.

BACKGROUND OF THE INVENTION

This compound, (±)3-deazaaristeromycin (compound VI), also known as (±)-4-amino-1-[1α,2β,3β,4α)-2,3-dihydroxy-4-(hydroxymethyl)cyclopentyl]-imidazo[4,5-c]pyridine, is a carbocyclic analog of adenosine and was found to inhibit adenosylhomocysteine hydrolase. Furthermore, it is noted that carbocyclic adenosine has no antiviral activity. Substitution of the 3-deazaadenine moiety for adenine in this compound gives a reversible inhibitor of the hydrolase more potent than 3-deazaadenosine and which has antiviral activity.

Prior Art Statement

U.S. Pat. No. 3,919,193 Mian et al—3-deazaguanosine and related compounds useful as antiviral agents.

U.S. Pat. No. 4,148,888 Cantoni et al—3-deazaadenosine as an inhibitor of adenosylhomocysteine hydrolase with antiviral activity.

U.S. Pat. No. 4,210,639 Chiang et al.—5'-deoxy-5'-(isobutylthio)-3-deazaadenosine, method of making same and its antiviral effect on rous sarcoma virus and gross murine leukemia virus.

SUMMARY OF THE METHOD OF PREPARATION

This invention relates to a procedure for the preparation of a potent new antiviral agent—the carbocyclic analog of 3-deazaadenosine ((±)-4-amino-1-[1α,2β,3β,4α)-2,3-dihydroxy-4-(hydroxymethyl)cyclopentyl-]imidazo[4,5-c]pyridine), compound VI. This compound is of interest because it is a potent antiviral agent and is an inhibitor of adenosylhomocysteine hydrolase.

In accordance with the practice of this invention, 2,4-dichloro-3-nitropyridine is allowed to react with (±)-(1,4/2,3)-4-amino-2,3-dihydroxycyclopentanemethanol in the presence of triethylamine to give (±)-(1,4/2,3)-4-(3-nitro-2-chloro-4-pyridylamino)-2,3-dihydroxy-1-cyclopentanemethanol (compound II). The nitro group of this pyridine was reduced with hydrogen and Raney nickel catalyst to the corresponding diamino compound, (±)-(1,4/2,3)-4(3-amino-2-chloro-4-pyridylamino)-2,3-dihydroxy-1-cyclopentanemethanol (compound III), which was cyclized to the 3-deazapurine, (±)-4-chloro-1-(1α,2β,3β,4α)-2,3-dihydroxy-4-(hydroxymethyl)cyclopentyl)imidazo[4,5-c]pyridine (compound IV) with triethyl orthoformate in N,N-dimethylacetamide using acid catalysis. The chloro group of compound IV was displaced with hydrazine and the resulting hydrazine compound, (±)-4-hydrazino-1-(1α,2β,3β,4α)-2,3-dihydroxy-4-(hydroxymethyl)cyclopentyl)imidazo[4,5-c]-pyridine (compound V) was cleaved with Raney nickel catalyst in water to the desired carbocyclic analog of 3-deazaadenosine (compound VI).

EXAMPLE 1

(±)-1,4/2,3)-4-(3-Nitro-2-chloro-4-pyridylamino)-2,3-dihydroxy-1-cyclopentanemethanol (II)

A solution of (±)-(1,4/2,3)-4-amino-2,3-dihydroxy-1-cyclopentanemethanol (294 mg, 2 mmol) and 2,4-dichloro-3-nitropyridine (1.12 g, 5.8 mmol) in 100 ml of absolute ethanol (dried over 3 A molecular sieves) containing triethylamine, 1 ml., was protected from moisture and refluxed overnight. Thin layer chromatography showed that the reaction was complete. The solution was evaporated to dryness, and the last of the ethanol was removed by addition of water followed by evaporation. The residue was partitioned between water and chloroform. The water was extracted once with chloroform. Evaporation of the chloroform followed by crystallization from ethanol gave 450 mg (40%) of 2,4-dichloro-3-nitropyridine. Evaporation of the water solution followed by crystallization from ethanol gave 345 mg (56.8%) of desired product. M.p. 175°–177° with softening from 170° (meltemp, uncorrected); homogeneous by tlc (3CHCl$_3$:1 MeOH); U.V.: pH 1: 248 (14.3), 268–274 (sh), 355 (1.97); pH 7: 248 (17.3), 375 (2.51); pH 13: 248 (17.3), 35 (2.51); NMR (DMSO-d$_6$), 2.2 (br m, H$_4$, +H$_{5'}$), 3.4 (d, CH$_2$OH), 3.7 (m, H$_{1'}$, H$_{2'}$, H$_{3'}$), 4.6 (br m, OH), 7.05 (d, H$_4$), 7.15 (d, NH), 8.0 (d, H$_5$).

EXAMPLE 2

(±)-4-Chloro-1-(1α,2β,3β,4α)-2,3-dihydroxy-4-(hydroxymethyl)cyclopentyl)imidazo[4,5-c]pyridine (IV)

A solution of compound III, 3.6 g (11.8 mmoles) in 250 ml of ethanol with Raney nickel, 1 g., was hydrogenated at atmospheric pressure and room temperature. As soon as hydrogen uptake stopped, the catalyst was removed by filtration through Celite. The catalyst was washed with fresh ethanol, and the combined filtrates were evaporated to dryness. The residue was dissolved in a mixture of dimethylacetamide, 40 ml, triethylorthoformate, 80 ml, and 12 N HCl, 2 ml. The solution was stirred overnight at room temperature before being evaporated to dryness in vacuo without heat. It was then evaporated with toluene in vacuo. A solution of the residue in 50% aqueous acetic acid (50 ml) was stirred at room temperature for 4 hours, evaporated in vacuo without heat, dissolved in water and evaporated in vacuo to remove acetic acid. It was dried in vacuo overnight and dissolved in 10% ammonia in methanol, 50 ml. The solution was stirred for 4 hours, evaporated to dryness, dissolved in ethanol and evaporated to dryness again. The residue was crystallized from water. The product was obtained in 2 crops; total yield, 1.71 g (51%); m.p. 219°–221°. U.V.: pH 1: 274 sh (6.16), 267 (6.4), 255–9 sh; pH 7: 275 (5.01), 267 (6.62), 258 (6.58); pH 13: 276 (4.96), 268 (6.56), 259 (6.42).

EXAMPLE 3

(±)-4-Amino-1-[1α,2β,3β,4α)-2,3-dihydroxy-4-(hydroxymethyl)cyclopentyl]imidazo[4,5-c]pyridine (VI) hydrochloride A solution of compound IV, 1.59 g (5.6 mmoles) in 95+% hydrazine, 48 ml, was refluxed under nitrogen for 1 hour. The solution was evaporated to dryness in vacuo, dissolved in water and evaporated again. A solution of the residue in oxygen-free water was stirred under nitrogen with Raney nickel at reflux for one hour. The mixture was filtered hot, and the catalyst was washed with boiling water. The combined filtrates were evaporated to dryness, and the residue recrystallized from water using charcoal. The product was collected, washed with water and dried in vacuo: 670 mg (40.1%) m.p. 236°–238°, with darkening from 230°. Two additional crops were obtained, 391 mg, total yield, 1.06 g (63.5%); U.V.: pH 1: 262 (10.1), 268 (9.84); pH 7: 263 (10.3), 268 sh; pH 13: 267 (10.4).

Calcd for C$_{12}$H$_{16}$N$_4$O$_3$.HCl: C, 47.92; H, 5.70; N, 18.63. Found: C, 47.89; H, 5.82; N, 18.51.

We claim:
1. A process for the production of (±)3-deazaaristeromycin, which comprises:
   (1) reacting 2,4-dichloro-3-nitropyridine with (±)(1,4/2,3)-4-amino-2,3-dihydroxy-1-cyclopentanemethanol to give (±)-(1,4/2,3)-4-(3-nitro-2-chloro-4-pyridylamino)-2,3-dihydroxy-1-cyclopentanemethanol (compound II) in an equimolar reaction in the presence of triethanolamine;
   (2) subsequently reducing compound II to (±)-(1,4/2,3)-4(3-amino-2-chloro-4-pyridylamino)-2,3-dihydroxy-1-cyclopentanemethanol (compound III) by hydrogen and Raney nickel catalyst;
   (3) acid catalyzed cyclization of compound III to (±)-4-chloro-1-(1α,2β,3β,4α)-2,3-dihydroxy-4-(hydroxymethyl)cyclopentyl)imidazo[4,5-c]pyridine (compound IV) with triethylorthoformate in N,N-dimethylacetamide with an acid catalyst;
   (4) displacing the chloro group of compound IV with hydrazine to produce (±)-4-hydrazino-1-(1α,2β,3β,4α)-2,3-dihydroxy-4-(hydroxymethyl)cyclopentyl)imidazo[4,5-c]pyridine (compound V);
   (5) cleaving said hydrazino compound V to produce (±)-4-amino-1[1α,2β,3β,4α)-2,3-dihydroxy-4-(hydroxymethyl)cyclopentyl]imidazo[4,5-c]pyridine (compound VI) under a nitrogen blanket with Raney nickel under a reflux.

* * * * *